US006444261B1

(12) United States Patent
Plaksine et al.

(10) Patent No.: US 6,444,261 B1
(45) Date of Patent: *Sep. 3, 2002

(54) STORAGE-STABLE PARTICLE, IN PARTICULAR CARRIER FOR CARRIER-BOUND REACTIONS, AND METHODS OF PRODUCING SAID PARTICLE

(75) Inventors: Dmitri Plaksine, Jülich (DE); Elena Gromakovskaia, Jülich (DE); Christoph Erhardt, Jülich (DE)

(73) Assignee: Abion Beteiligungs-und Verwaltungsgesellschaft mbH, Jülich (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/068,886
(22) PCT Filed: Nov. 22, 1996
(86) PCT No.: PCT/EP96/05161
  § 371 (c)(1),
  (2), (4) Date: Jul. 20, 1998
(87) PCT Pub. No.: WO97/19354
  PCT Pub. Date: May 29, 1997

(30) Foreign Application Priority Data

Nov. 22, 1995 (DE) .......................... 195 43 556
Jan. 20, 1996 (EP) ............................ 96100821

(51) Int. Cl.$^7$ .................. G01N 33/546; B01J 13/02; B05D 7/00; B32B 15/02; B32B 17/02
(52) U.S. Cl. ............... 427/213.31; 427/213.32; 427/213.33; 427/213.34; 427/213.35; 427/213.36; 428/402.2; 428/402.21; 428/402.22; 435/177; 435/178; 435/179; 435/180; 435/181; 435/182; 436/528; 436/529; 436/530; 436/531; 436/532; 436/533; 436/534; 436/535; 530/812; 530/813; 530/814; 530/815; 530/816; 530/817

(58) Field of Search ................. 427/213.31, 213.32, 427/213.33, 213.34, 213.35, 213.36; 428/402.2, 402.21, 402.22; 435/176, 177, 178, 179, 180, 181, 182; 264/4.1, 4.3, 4.33, 4.4, 4.7; 436/528, 529, 530, 531, 532, 533, 534, 535; 530/812, 813, 814, 815, 816, 817

(56) References Cited

U.S. PATENT DOCUMENTS 5,069,936 A * 12/1991 Yen .............................. 264/4.1
5,308,701 A * 5/1994 Cohen et al. ........... 428/402.22

FOREIGN PATENT DOCUMENTS

| EP | 0 184 710 | 6/1986 |
| EP | 0 321 008 | 6/1989 |
| WO | 92 08134 | 5/1992 |

* cited by examiner

Primary Examiner—Nathan M. Nutter
(74) Attorney, Agent, or Firm—Jacobson Holman, PLLC

(57) ABSTRACT

A particle resistant to storage of at least one first and at least one second component, wherein said second component of at least one crosslinkable polymer as a shell at least partially envelops and/or encloses said first component as a core and said first component has at least one ascertainable property, obtainable by reacting said first component with the crosslinkable polymer and subsequently reacting the formed product with a crosslinking agent such that the first component with resistance to storage remains within the second component.

16 Claims, No Drawings

STORAGE-STABLE PARTICLE, IN PARTICULAR CARRIER FOR CARRIER-BOUND REACTIONS, AND METHODS OF PRODUCING SAID PARTICLE

This is a 371 of PCT/EP96/05161, filed Nov. 22, 1996, now abandoned.

The object of the present invention is a particle resistant to storage, especially a particulate carrier for carrier-bound reactions, detection and/or isolation processes, a process for the production of this particle resistant to storage, and uses of the particle according to the invention.

Particulate carriers consisting of a solid core and a polymer are known as such and have already been used for many purposes. In particular, such particles have been used for immunoassay markers to bond a solid core by means of polymers, e.g., biopolymers, to an affinity component. As particulate material especially sols of metal particles, e.g., magnetic iron particles of colored gold particles, nonmetallic particles, e.g., selenium, coal dust, $SiO_2$ or ceramic particles, corpuscles or even latex particles of another polymer with different (bonding) properties have been used.

Thus, U.S. Pat. No. 4,230,685 describes an improvement of the bonding of specific binders to magnetic particles, whereby a particle is coated with an acrylate polymer or a polysaccharide, whereby protein A is bonded to this coating by glutaraldehyde.

U.S. Pat. No. 4,452,773 describes the production of magnetic iron-dextran microparticles. These particles have a size of from 100–700 Å, in particular 300–400 Å. A large number of the particles are colloidal and ferromagnetic with a dextran shell. The obtained particles are functionalized by periodate oxidation.

EP-B-452,342 concerns super-paramagnetic particles coated with polysaccharides having colloidal size. The particles can be bonded to additional groups. By sorting out the particle mixture into size subtractions having uniform magnetizations there are obtained compositions having homogeneous properties with regard to the retardance thereof within a magnetic field. The possibility to separate with respect to size is mentioned. Preferred are coatings from polysaccharides or proteins. Polysaccharides are functionalized by periodate oxidation. In addition, functionalization with bromocyanogen is possible. The bonding of the protein shell to particular molecules can be effected by side chain amino groups or sulfhydryl groups.

DE-A-40 37 724 relates to devices for immunoassays in which a direct or indirect markers are used. Direct markers are preferred as they do not require additional steps to visualize test results. Examples for direct markers are metal sols, dye sols, latex particles, color indicators, colorants located in liposomes, and nonmetal sols such as a carbon sol. Another aspect of DE-A-40 37 724 relates to an immunochemically active marker. Then, a coal dust particle is bonded adsorptively to a ligand or a ligand conjugate. The sensitivity of the test for, e.g., human choriongonadotropine hCG is denoted as 25 mIU/ml (IU=international unit).

EP-A-0,410,893 describes a process for the determination and recognition of an antibody within biological fluids directed against a specific antigen. The listed insoluble carrier particles comprise cells, gelatin particles, microcapsules, organic polymers, inorganic fine particles, or colloidal particles of metal or metal compounds being finely dispersed with bovine serum albumin or cholesterol.

Also EP-A-0,032,270 describes a quantitative and/or qualitative determination of an immunologic component using one or several marked compounds being obtained by a direct or indirect coupling of such component(s) to particles from an aqueous dispersion of a hydrophobic dye or pigment or polymeric cores being coated with such dyes or pigments.

EP-0,321,008 relates to a process for the determination of one or several components of a reaction between a specifically bonding protein and the corresponding bondable substance within a sample, the mutual activity of such components and of at least one marked component being obtained by coupling or adsorbing sol particles of the marking directly or indirectly to the component. Preferred sol particles are phosphorus, carbon and/or silicon. Agglutination and aggregation can be prevented by covering the particles with macromolecules containing polar groups such as proteins, poly(ethylene glycol), polymeric carbohydrates, poly(vinyl alcohols), and similar ones. Suitable protective proteins are antigens, antibodies, and anti-antibodies. Immunochemically inert materials such as, e.g., albumin, poly (ethylene glycol), or other polar macromolecules may be used as well. The test sensitivity, e.g., with respect to rabbit immunoglobulin G, is specified as 1.5 ng absolute.

EP-0,298,368 concerns a process for carrying out a diagnostic immunoassay by using colloidal iron metal containing particles having a conjugate attached to them being capable of recognizing specifically the analyte to be determined. The test sensitivity for hCG is in the mIU/ml range.

EP-A-0,280,560 discloses Streptococcus A antigen antibodies being bonded covalently to core/shell polymer particles, the shell being formed from poly(mp-chloromethylstyrene) and the core from poly(styrene-co-2-acetoacetoxidethyl methylacrylate), containing Oil Red EGN within the core to obtain a agglutination reagent.

U.S. Pat. No. 4,452,886 describes the polymerization of lysine with glutaraldehyde and Congo red to colored particles. The test sensitivity for hCG is in the 1000 IU/ml range.

W. P. Collins describes in his book "Alternative Immunoassays", John Wiley & Sons, Chichester, N.Y., etc., in the chapter "Disperse Dye Immunoassay (DIA)" on page 48–49 the advantages of particle markers and points out the significance of the essential parameters such as particle size, distribution and form, solubility in organic solvents, colloid stability, and bonding capacity, e.g., for antibodies. The test sensitivities mentioned by him are in the mIU/ml range. The conjugates are stable for at least 15 months if they are stored in the lyophilized state at −20° C. or 4° C.; aqueous conjugates should be consumed within 6 days after preparation.

JP-A-0686771 relates to encapsulated toners and the production thereof.

The inert cores described in the art have been suffering from obvious drawbacks. In case the cores are polymerized therein, the desired core property is impaired too much. In case the polymer is adsorbed on the core with a subsequent covalent or other bonding of the affinity component, the bonding of the core in most cases is too weak, so that the stability is not ensured at longer term. In addition, by employing the methods according to the art only the bonding of one or a small amount of reactive and affinity components is achieved.

The object of the invention consists of providing stable particles with characteristic usable properties, especially marking properties, allowing, if necessary, also numerous reactive components at the same time to be stably bonded thereon. Stability should in particular also comprise a storage at longer terms.

The present invention provides a particle resistant to storage, especially a particulate carrier according to the features of claim 1. Dependent claims 2–18 relate to preferred embodiments of the according to the invention particle. Claim 19 together with the appropriate dependent claims 20 and 22 relate to a process for the production of the particle according to the invention resistant to storage. Claims 23–31 relate to uses of the particle according to the invention.

The particle according to the invention resistant to storage is especially destined for carrier-bound reactions, detection and/or isolation processes. It consists of at least a first and a second component, the particle being suitable to be provided with a reactive component, especially a specific reactive component. The second component consists of a crosslinkable polymer and forms more or less a shell enveloping and/or enclosing the first component as the core at least partially.

The first component has at least one ascertainable property. On the second component there may be arranged reactive components. The particle resistant to storage is characterized by its manufacturing process and available by reacting the first component with the crosslinkable polymer, thereafter reacting the formed product with a crosslinking agent such that the first component is arranged within the second component resistant to storage.

Preferably, the reaction conditions are adjusted such that the first component is enveloped and/or enclosed by the second component in a reticular manner.

The second component forming the carrier according to the invention is preferably a polymer having active or activatable functional groups being able to react in one respect with the crosslinking agent or else with the reactive components or with both of them. The polymer forming the second component of the carrier according to the invention can also be produced from several crosslinkable polymers and/or crosslinkable monomers. Then, the polymer can be produced from proteins and/or polyamides with functional groups. In principle, also other polymers such as biopolymers or rather monomers are possible as far as crosslinking is achievable. Preferably, the second component is crosslinkable with at least bifunctional compounds.

Preferably polymers are used which stabilize the aqueous suspension of component 1 adsorptively, that is, especially polar polymers.

The reactive components arranged at the second component of the particle according to the invention are especially molecules or molecular groups possessing affine properties towards other substances. These include especially enzymes and substances interacting with enzymes. Then, on the one hand the substrate or on the other hand the enzyme can be arranged at or on the second component as the reactive component. Antibody/antigen, biotin/streptavidin behave likewise. Streptavidin or biotin in form of a specific reactional component bonded stably to the dye possesses the advantage the dye is universally usable as a co-reactant for biotinylated components or those coupled with streptavidin. These can on their part possess entirely different functions, e.g., act again specifically against another component or as a catalyst. In addition, nucleic acids of RNA or DNA types are usable within the meaning of the carrier according to the invention. The nucleic acids are able to hybridize with the corresponding complementary or partially complementary strands depending on the stringency of the reaction conditions and to form stable complexes. Consequently it is possible to identify specific nucleic acid strands within a sample to be investigated and to process further on the basis thereof. In addition, combinations of the reactive components can be arranged at or on the second component. Then, in accordance with the invention one obtains carriers which are applicable for different problems.

By selecting the crosslinking agent and the concentration thereof and adjusting specific processing conditions, the crosslinking reaction can be controlled such that the second component envelops the first component more or less in a molecular net, the meshes thereof possessing a narrow mesh size distribution.

At the same time, by means of the processing conditions of crosslinking there can be adjusted the number of free binding sites at the surface of the particle which remain free due to the binding of the at least bifunctional crosslinking agent with only one function to the surface for an additional binding, especially of reactive components. The created number of binding sites can be used completely or partially with a defined portion after a partial saturation.

In particular, by means of the processing conditions the thickness of the shell can be adjusted, whereby the homogeneity thereof subsequently still can be increased by a fractionation. A multi-step covering process can still improve the inclusion of the first component.

The first component of the particle in accordance with the invention do possess at least one ascertainable property component 2 and/or the reactive components bonded thereon do not possess with regard to the quality thereof, such as absorptivity or emissivity of electromagnetic waves, mass, magnetism, dielectricity, radioactivity, size and/or density.

As ascertainable properties the core as the first component of the carrier according to the invention can possess there are understood also a pharmacological-biological effect as well as a catalytical effect or combinations of these. So, for example the absorptivity or emissivity of electromagnetic waves can be produced by respective chromophores or fluorophores. The properties mass, size, and density are interconnected physically and can be adjusted accordingly by, e.g., particles with a higher specific density. The property of size can be used advantageously for agglomeration and the property of mass for gravimetry. Agglomeration is advantageous for the specific precipitation of components in solutions or microemulsions. The first component can be provided with the property of radioactivity by radioactive marked structures. Similarly the other specified properties can be connected with the first component. The first component can as well be a capsule containing liquids or particles which cannot be enclosed sufficiently (for example particles being extremely small or instable in solution).

In an advantageous design of the carrier according to the invention the carrier is such that the first and second components are connected separably with each other. The connection between first and second components is effected by enclosing the first component within the second one. Basically, it is possible to expose the first component by removing, if necessary, the second component to facilitate a detection of the properties connected with the core by measurement techniques. Removing the second component can be performed, e.g., in case of proteins by appropriate proteolytic enzymes. These degrade the shell such that the core remains. The latter can further be treated in accordance with its property to be measured. In addition, it is possible to dissolve the core from the connection of first/second component by treating it with a medium wherein the core dissolves preferably, so that in the end an "empty" shell remains, or to dissolve the complete particle by means of a total solvent. So, e.g., if a dye soluble in ethanol is enclosed by the second component, it is possible to treat with the solvent and to measure the obtained ethanolic solution spectroscopically. If the conditions are standardized and, if necessary, calibrated, a corresponding discoloration can be used as a quantity for quantitative determinations.

In addition to the individual particulate carriers resistant to storage the embodiments thereof also possess a great significance in performing methods of application. Then, the particulate carriers resistant to storage present themselves in majority in form of populations. For the application of the particles according to the invention the carriers are preferred to be present in populations being distinguished by a narrow size distribution of the individual carrier particles according to the invention.

It is especially preferred that the population possesses carrier particles having as well a narrow range of the shell size distribution as a narrow range of the core size distribution and consequently a narrow range of the shell/core size distribution. Also for other properties there is desired a homogenous distribution, e.g., of the color intensity or the magnetizability, for the core, especially for the entire particle.

In the practical use of the particle according to the invention as a carrier it is advantageous to arrange a high concentration of reactive components at or on the second component. Because of this there can be achieved relatively high bonding constants to corresponding complementary structures in immunoassays, although the individual reactive component and its corresponding complementary structure possibly possess only an average bonding constant. However, due to the multiplicity of binding sites the effectiveness of bonding (avidity) is increased.

A process for the production of the carrier according to the invention comprises the steps of reacting the first component with a crosslinkable polymer at least one time. Then, the polymer can be adsorbed physically at the surface of the first component. The crosslinkable polymer will then, subsequently to further processing steps, form the second component. This is effected by a treatment with crosslinking agent. As crosslinking agents there are possible especially bifunctional molecules such as glutardialdehyde, dicarboxylic acids, acrylates, methacrylates. Then, the crosslinking agents having olefinic groups are activatable by, e.g., photo reactions or other free-radical chain reactions. The functional molecules can crosslink the polymers in particular via condensation or addition reactions.

Optionally, the first component before the treatment and/or the intermediate product together with the second component and/or the particle can be subjected to a separation by size and/or by another property to achieve a distribution of size and/or of another property as homogenous as possible. It is preferred to perform the treatment of the first component with polymers two to three times, and it is especially preferred to perform a separation by sizes.

The process is particularly advantageous as it is possible to homogenize the first component and to adjust the concentration thereof within the suspension initially, irrespective of a reaction. Depending on the first component used there can be employed standard processes for the homogenization and stabilization of the suspension. Preferably the second component is used to stabilize the suspension if it is a polar compound with a sufficiently good adsorption at the first component. The ratio of the concentrations of the first and the second components is selected such that a suitable thickness of the shell is achieved by adsorption. In the multistep process the thickness of the shell is selected preferably thin. Other parameters such as time and temperature can be used as well to influence the adsorption.

Thereafter, the intermediate product can be re-homogenized. To achieve a good crosslinking of the shell, especially within the inner area near by the first component, the crosslinking component is added in an excess of several orders of magnitude. In addition, the effect of the crosslinking component can be influenced by other parameters, in particular the contact time as well as the number of formed reactive groups on the surface due to single-side bonded crosslinking molecules which number can be reduced by partial blocking subsequently.

The carriers according to the invention are preferably used in assay techniques such as immunoassay, solid-phase assays and/or chromatographic assays. In addition, they can be used as vehicle for the affinity transport of effective substances if for example pharmacologically active substances as the first component are enclosed by the second component. As affinity transport there is to be understood, e.g., transports of pharmacologically active substances by means of antibodies being located at the second component and bonding specifically to a particular target structure.

Particles with a radioactive core can be used advantageously, too, as they act or are concentrated due to the affinity transport above all at the location of application, and therefore lower overall radioactivity doses can be used, whereby a systemic strain can be kept within narrow limits.

The use of the particulate carriers resistant to storage according to the invention as a catalyst for chemical reactions is advantageous as well. Accordingly, for a rapid intermixture of the carrier-bound catalyst (biocatalyst) with the reaction mixture there can be used a magnetic core, the weight of which subsequently provides a rapid separation.

The invention will be illustrated further by the following examples.

EXAMPLE 1

Preparation of a Sudan IV dye particle having a high loading of streptavidin as the specific reactive component for biotinylated components.

1. Peptization 10.0 g of Sudan IV were added to 100 ml of PBS buffer (Phosphate Buffer Solution) with 2% of BSA (Bovine Serum Albumin) sterilized by filtration above 2 $\mu$m) and agitated at high agitation speed to yield a homogeneous suspension. After that, the suspension was coarse-filtered (filter paper BioRad, model 543).

The suspension was distributed over two centrifuge tubes and centrifuged in a-centrifuge precooled to 4° C. at 1000 rpm, at 2000 rpm, and at 3000 rpm for 5 minutes, resp. Subsequently a second filtration was performed.

2. Crosslinking and Activation 50 ml of a 50% aqueous glutaraldehyde solution were brought to room temperature (hood) and adjusted to pH 7.3 with about 11 ml of 0.3 M $Na_2HPO_4$ buffer (verification with pH meter). Subsequently there were added 25 ml of PBS buffer and 5 ml of a 1:1 mixture of PBS buffer and bidistilled $H_2O$ (in the reaction solution about 1.5 M of glutaraldehyde or 2.8 M of aldehyde groups, about $1.5 \times 10^{-4}$ M of BSA or with 300 amino acids per BSA about $4.5 \times 10^{-2}$ M of reactive amino acid, that is, about 60 aldehyde groups per amino group). The entire solution (pH 7.3) was sterilized by filtration (0.2 $\mu$m).

To 20 ml of this glutaraldehyde buffer solution, resp., there were added with turbulent mixing (vortex) 20 ml of the peptized Sudan IV suspension (4 parallel preparations), resp., and shaken for 4 hours at room temperature.

40 ml of the activated suspension, resp., was stabilized in the centrifuge tube with 2.2 ml of a 2% BSA solution (0.2

μm filtered). Subsequently the preparations were centrifuged at 2500 rpm for 5 minutes and coarse-filtered thereafter.

3. Column Purification (Gel Filtration)

A column with CL 4B Sepharose (Parmacia) was well regenerated and equilibrated for at least one hour with PBS buffer at room temperature, then the round filter was fed and the supernatant buffer volume was sucked off or drained. The 160 ml of stabilized suspension were fed to the column and the column, was covered. After infiltrating (about 25 minutes) the brim of the column was rinsed with PBS buffer and a pump was turned on.

For fractionation there were prepared-conical 12 ml tubes with graduations for the receiving volumes:

Tube no. 1 to 10 and 23 to 30 each 4 ml; no. 11 and 22 4.5 ml; no. 12 and 21 5 ml; no. 13 and 20 5.5 ml; no. 14–19 6 ml.

As soon as the red solvent front appeared in the outlet the fractions were collected. The gel filtration took about 30 minutes.

Each 5 μl of each fraction were diluted with each 5 ml of PBS buffer (1:1000) and mixed turbulently (Vortex) for the optical-visual evaluation of the color intensity. The evaluation of the fractions with regard to the color intensity thereof resulted in a broad central peak area with high color intensity and clearly deceasing coloration in the fractions before and after it. The broad peak area of about 140 ml was used. The fractions thereof were pooled, distributed to 3 50 ml tubes, centrifuged at 2500 rpm for 5 minutes, and subsequently coarse-filtered.

(If necessary, steps 2 and 3 were repeated once or several times for a thicker and/or more secure shell.)

4. Conjugation with Streptavidin as Specific Reactive Component 100 mg of streptavidin were dissolved in 6 ml of BPS buffer, for testing the quality the protein concentration was determined by means of the optical density at 280 nm and compared with the manufacturer's specification. The streptavidin solution was given into a 6 mm dialysis tubing and dialyzed against 1 l of PBS buffer at 4° C. over night. The solution was given into tubes, the tubing was rerinsed with 4 ml of PBS buffer, and the protein concentration was again determined with the $OD_{280}$ to verify the concentration. The streptavidin solutions were centrifuged with 4000 rpm for 5 minutes and the supernatant, after another determination of $OD_{280}$, was used for conjugation.

The coarse-filtered suspension of the Sudan IV dye coated with crosslinked BSA with active residual aldehyde groups was coupled in 4 preparations with the streptavidin supernatant as follows:

About 3 ml streptavidin solution (with about 11 mg/ml of protein) was given into 50 ml tubes. To this were given about 30 ml of the suspension with turbulent mixing (that is, about 33 mg of streptavidin per 33 ml of suspension). The solutions were kept in the overhead shaker at room temperature over night, and centrifuged with 2500 rpm at the next morning for 5 minutes, and coarse-filtered subsequently. The overall suspension volume was about 130 ml thereafter.

5. Column Purification CL-6B Sepharose Color Test

The column was prepared and equilibrated as described under 3. Infiltration of the 130 ml of suspension took about 25 minutes, gel filtration about 30 minutes. The tubes for fractionation were prepared as under 3. The fractions were either diluted as under 3. or assessed only optically-visually. In case a higher color quality was required, the fractions were tested with a 1:50 dilution in a test according to DE-A1-195 00 862, example 1, with respect to the suitability thereof. To a column with a gel bed with monoclonal murine-anti-human-IgG antibody were given 250 μl of a 1:5000 diluted pooled serum initially containing 84 IU/ml human-anti-tetanus IgG (sensitivity 1.7 mIU/ml, absolutely about 0.4 mIU, International Units), followed by 250 μl of a solution of 5 μg/ml biotinylated tetanus toxoid. After adding 250 μl of the 1:50 diluted suspension of the dye coupled to streptavidin a distinct coloration had to be visible. The central pooled range having a high absorption comprised a broad peak area of about 100 ml, for lower requirements the two shoulder areas, left hand and right hand, of 30 ml, resp., were pooled separately, too. After turbulent mixing (Vortex) and gel filtration both pools were stored at 4° C. (if necessary, over night) until stabilization was achieved.

6. Stabilization

A 20% BSA solution in PBS buffer was sterilized by filtration with 0.2 μm. Into the 50 ml tubes rinsed with BSA solution there was given to 22 ml of 20% BSA solution with turbulent mixing (Vortex) 18 ml of the coarse-filtered suspension. Subsequently, the suspensions were coarse-refiltered.

7. Storage

In well sealed 50 ml tubes the suspension stabilized with 0.09% of sodium azide is stable at 4° C. for at least 12 months with stable absorption value.

8. Properties

Compared with an average size of about 50 nm of the Sudan IV particles the size is from about 51 to 200 nm after a single-coating and from 300 to 400 nm after a double-coating.

EXAMPLE 2

Immunoassay using the inventive particulate carrier materials resistant to storage according to example 1.

Semi-quantitative and quantitative measurement of the tetanus vaccination status; that is, of the anti-tetanus-IgG concentration in the blood.

a) Semi-quantitative Test

For the semi-quantitative test directed towards the visual effect there was used a reaction column for simultaneous multi-measuring according to DE-A1-195 00 862 with 3 areas.

The bottom reaction area (comparative area) of the reaction column is loaded with protein G and bonded thereon with a defined amount of anti-tetanus human IgG corresponding to a sufficient inoculation in IU (International Units) of the blood volume within the capillary for the blood application.

For this a pooled serum was diluted accordingly, and the total human-IgG including the tetanus-specific one was bonded to the protein G of this reaction area in the flow (protein G coupled with CNBr activated agarose, see DE-A-195 00 862, example 2 given therein.)

The middle negative control area contains CNBr activated Sepharose 4B with covalently coupled BSA.

The top reaction area (test area) of the reaction unit contains exclusively protein G coupled with CNBr activated agarose.

A defined blood amount is applied to the column by means of a capillary. After washing with a washing buffer; 250 μl of a solution of 5 μg/ml of biotinylated tetanus toxoid (biotinylation level 50) are applied in washing buffer. After an additional washing a 1:20 washing buffer dilution of the streptavidin dye emulsion is applied and washed again.

The total human IgG of the sample is bonded within the test carrier bed during its flow. In both areas, the test area and the comparative, area, during flow there is bonded an amount of the anti-tetanus-human IgG bonded before, resp., corresponding with biotinylated tetanus toxoid. Unspecifically bonded proteins are washed out by subsequent buffer. Thereafter, during flow of the dye emulsion in the test area and the comparative area there is bonded an amount of streptavidin coupled dye corresponding with the amount of tetanus toxoid. Also in this case unspecifically bonded protein is washed out by the washing buffer. Nothing is bonded within the negative control area.

The semi-quantitative evaluation takes place by visual comparison of colors. In case the coloration of the test area equals or exceeds that of the comparative area, the vaccination status is sufficient. In case it is weaker, one should inoculate, that is, the more urgently, the more important the color difference is (finer graduations of comparative areas can be produced according to medical or WHO information, e.g., two years of protection remaining, five years of protection remaining, inoculation recommended, inoculation strongly recommended. An alternative consists in evaluating the penetration depth of the colors into the test area with corresponding marking. Then, one comparative area can be omitted or used as protection.)

b) Quantitative Test

For this only one test area is required, however, for certainty positive and negative control areas can be incorporated.

The area is loaded with murine-anti-human IgG according to DE-A-195 00 862, example 2. The application sequence and the reactions are such as described under lit. a). Evaluation is performed by photometric absorption measurement at 520 nm or 492 nm after eluting with an alcoholic solution.

Eluting with alcohol is necessary as the dye marker due to the great number of binding sites adheres so stably to the gel bed it cannot be separated from the gel bed like other markers by means of pH variations or by displacement by a concurrence molecule, even not partially, but in this case exclusively by dissolving.

The test sensitivity is in the mIU/ml range for both evaluations or anti tetanus human IgG. Absolutely, without further optimization of the test, amounts of less than 10 pg IgG can be determined qualitatively (visually) and quantitatively, with enriching within the column even less (pg/ml range).

Current quality control yielded an emulsion stability of at least 12 months.

EXAMPLE 3

Synthesis of an activated dye particle

To 20 ml of BSA solution within a concentration range of 1 to 50 mg/ml in 0.01–0.2 M phosphate buffer solution, pH 6–8.5, there was added from 0.1 to 2 g carbon. The mixture is mixed by a magnetic agitator or a Vortex mixer until a sufficient adsorption of the protein (peptization) has occurred. The obtained suspension is centrifuged at 6000×g for 5 to 10 minutes.

The carbon particles of from 50 to 350 nm, on which BSA is adsorbed, are activated with glutardialdehyde during the next step. The glutardialdehyde concentration for this ranges from 1 to 25%, the activation time is from 20 to 120 minutes.

The activated suspension is purified by centrifuging 3 to 4 times and by gel filtration with Sepharose 6B, 4B, 2B, CL-6B, CL-4B, CL-2B, Sephacryl S300, or with other gels (Toyoperl, Ultragel etc.), whereby the exclusion limit is not allowed to fall below $1 \times 10^6$ Dalton for globular proteins. Employing this method one obtains black dye particles. The preparation of other dye particles is performed in an analogous manner using instead of carbon, e.g., Sudan II for red, Sudan III for dark red, Sudan black for grey, tetrazoleformanzane violet for violet, neotetrazolediformazane for dark violet, and tetrazolediformanzane blue for blue. The working range for these conjugates in suspension is about 0.08%, based on the dry weight. The dye labels are produced by conjugating with antianalytes such as protein A, streptavidin or antibodies.

EXAMPLE 4

Serological determination of anti-HiV antibodies on a non-porous solid phase by means of a protein A carbon conjugate.

As solid phase there were employed polystyrene-ELISA plates with adsorbed synthetic peptides of HIV-1 and HIV-2. Subsequently, in a dilution series a rabbit-anti-HIV serum was added. After an incubation of 15 minutes and a purifying step there was added protein A carbon conjugate and the resulting spot was read after 15 min following a purifying step.

In parallel, analogous experiments were conducted with purchased protein A gold colloid (40 nm particle size) and protein A-POD. Comparison of the visual evaluation yielded a sensitivity of both of the other markers for a dilution of 1/1280, for the carbon conjugate of 1/20480.

EXAMPLE 5

Determination of HCG with carbon conjugate with thin layer chromatography

A strip of 2×16 mm nitrocellulose is bonded to transparent 0.5 mm PVC. One end of the strip was bonded to a 1×1 cm piece of chromatography paper as suction element. In the middle of the nitrocellulose strip there was applied a solution of anti-HCG-antibody (1 mg/ml in phosphate buffer) with a Hamilton syringe. After 30 minutes it is blocked with a 1% casein solution (phosphate buffer with Tween) (one hour), thereafter purified and dried.

The HCG standard is diluted once with phosphate/Tween buffer, thereafter once again with urine of a healthy individual adding up to 0.1 Tween 20. 50 µl carbon conjugate with anti-HCG are added to 50 µl of this standard solution. The free end of the strip is dipped into this solution, the result being read off visually as a black line after 2 to 3 minutes. The sensitivity of 50 mIU/ml is sufficient for a pregnancy test after one week.

What is claimed is:

1. A reactive particle comprising:
   a) a shell of crosslinked polymer, wherein the crosslinked polymer is bound to at least one reactive component selected from the group consisting of an enzyme, an enzyme substrate, an antibody, an antigen, biotin, streptavidin, RNA, and DNA, the crosslinked polymer reticularly enclosing
   b) a core of material having at least one property selected from the group consisting of absorptivity of electro magnetic waves, emissivity of electromagnetic waves, mass magnetism, dielectricity, radioactivity, size distribution, pharmacological activity, biological activity, and catalytic activity,
the particle produced by the process comprising the steps of:
   reacting at least one crosslinkable polymer, wherein the crosslinkable polymer is bound to the at least one reactive component, with the material having at least one property to produce an intermediate comprising (i) the crosslinkable polymer enveloping (ii) a core of the material followed by reacting the at least one crosslinkable polymer with a crosslinking agent, at a ratio crosslinking agent/crosslinkable polymer of at least 10/1, to crosslink the polymer to form a molecular network and, thereby, reticularly enclose the core.

2. The particle of claim 1, the at least one crosslinkable polymer is a biopolymer.

3. The particle of claim 2, wherein the at least one biopolymer is a polyamide.

4. The particle of claim 3, wherein the at least one crosslinkable polymer is bound to the at least one reactive component through at least one bi-functional compound covalently binding each of the crosslinkable polymer and the reactive component.

5. The particle of claim 3, wherein the at least one bi-functional compound is selected from the group consisting of a dialdehyde, a dicarboxylic acid, acrylate, and a divinylic compound.

6. The particle according to claim 3, wherein the at least one reactive component is covalently bound via a spacer to each of the shell and the core.

7. A process for the production of a particle having a core and a shell comprising the steps of:

reacting at least one crosslinkable polymer, wherein the crosslinkable polymer is bound to at least one reactive component selected from the group consisting of an enzyme, an enzyme substrate, an antibody, an antigen, biotin, streptavidin, RNA, and DNA, with a material having at least one property selected from the group consisting of absorptivity of electro magnetic waves, emissivity of electromagnetic waves, mass magnetism, dielectricity, radioactivity, size distribution, pharmacological activity, biological activity, and catalytic activity, to produce an intermediate comprising (i) the crosslinkable polymer enveloping (ii) the material followed by reacting the at least one crosslinkable polymer with a crosslinking agent, at a ratio crosslinking agent/crosslinkable polymer of at least 10/1, to crosslink the polymer to form a molecular network and, thereby, reticularly enclose the material and, thereby, effect said particle.

8. The process of claim 7, further comprising the step of fractionating the intermediate according to size.

9. The process according to claim 7, wherein the crosslinking is by condensation reaction, addition reaction, or substitution reaction.

10. In an assay comprising combining a carrier-bound agent with a test substance, wherein the carrier-bound agent selectively binds a target and is evaluated by qualitatively measuring a property of the carrier-bound agent, the improvement wherein the carrier-bound agent is the reactive particle of claim 1, and wherein the property measured is at least one property of the core.

11. The assay of claim 10, further comprising dissolving the shell of the particle by using a solvent, a change in pH, or a change in salt concentration, before measuring the at least one property of the core.

12. The assay of claim 10, wherein the properties of the core are magnetism and absorption to quantify.

13. A timed-release pharmacological agent comprising the reactive particle of claim 1, wherein the core material is a pharmacologically active substance, and wherein the shell dissolves over time after administration.

14. A biological agent comprising the reactive particle of claim 1, wherein the core is a biologically active substance, and wherein the shell dissolves over time when added to a liquid.

15. A vehicle for affinity transport of active substances comprising the reactive particle of claim 1.

16. A catalyst comprising the reactive particle of claim 1, wherein the core has magnetic properties for rapid intermixing and weight properties for rapid separation.

* * * * *